(12) United States Patent
Sjolin et al.

(10) Patent No.: US 9,903,958 B2
(45) Date of Patent: Feb. 27, 2018

(54) OBTAINING MEASUREMENT INFORMATION FROM AN EDGE-ON X-RAY DETECTOR AND DETERMINING THE ORIENTATION OF AN EDGE-ON X-RAY DETECTOR WITH RESPECT TO THE DIRECTION OF INCOMING X-RAYS

(71) Applicant: PRISMATIC SENSORS AB, Stockholm (SE)

(72) Inventors: Martin Sjolin, Stockholm (SE); Fredrik Gronberg, Stockholm (SE)

(73) Assignee: PRISMATIC SENSORS AB, Stockholm (SE)

( * ) Notice: Subject to any disclaimer, the term of this patent is extended or adjusted under 35 U.S.C. 154(b) by 0 days.

(21) Appl. No.: 15/505,303

(22) PCT Filed: Sep. 23, 2015

(86) PCT No.: PCT/SE2015/050994
§ 371 (c)(1),
(2) Date: Feb. 21, 2017

(87) PCT Pub. No.: WO2017/052431
PCT Pub. Date: Mar. 30, 2017

(65) Prior Publication Data
US 2017/0269234 A1  Sep. 21, 2017

(51) Int. Cl.
*G01N 23/04* (2006.01)
*G01T 1/16* (2006.01)
(Continued)

(52) U.S. Cl.
CPC ............... *G01T 1/16* (2013.01); *G01B 15/00* (2013.01); *G01T 7/005* (2013.01)

(58) Field of Classification Search
None
See application file for complete search history.

(56) References Cited

U.S. PATENT DOCUMENTS

| 4,937,453 A | 6/1990 | Nelson |
| 5,131,021 A | 7/1992 | Gard et al. |

(Continued)

FOREIGN PATENT DOCUMENTS

| DE | 102013219137 A1 | 3/2015 |
| EP | 1346689 A2 | 9/2003 |

(Continued)

OTHER PUBLICATIONS

International Search Report, dated Jul. 7, 2016, from corresponding PCT application No. PCT/SE2015/050994.

(Continued)

*Primary Examiner* — Hoon Song
(74) *Attorney, Agent, or Firm* — Young & Thompson

(57) ABSTRACT

There is provided a method for at least partly determining the orientation of an edge-on x-ray detector with respect to the direction of x-rays from an x-ray source. The method includes obtaining (S1) information from measurements, performed by the x-ray detector, representing the intensity of the x-rays at a minimum of two different relative positions of a phantom in relation to the x-ray detector and the x-ray source, the phantom being situated between the x-ray source and the x-ray detector and designed to embed directional information in the x-ray field when exposed to x-rays. The method also includes determining (S2) at least one parameter associated with the orientation of the x-ray detector with respect to the direction of x-rays based on the obtained information from measurements and a geometrical model of the spatial configuration of the x-ray detector, x-ray source and phantom.

25 Claims, 10 Drawing Sheets

(51) Int. Cl.
*G01T 7/00* (2006.01)
*G01B 15/00* (2006.01)

(56) References Cited

U.S. PATENT DOCUMENTS

| | | | |
|---|---|---|---|
| 5,434,417 | A | 7/1995 | Nygren |
| 5,469,429 | A | 11/1995 | Yamazaki et al. |
| 6,370,218 | B1 | 4/2002 | Toth et al. |
| 8,183,535 | B2 | 5/2012 | Danielsson et al. |
| 8,262,288 | B2 | 9/2012 | Shaughnessy |
| 8,622,615 | B2 | 1/2014 | Ren et al. |
| 2003/0058999 | A1 | 3/2003 | Mitschke et al. |
| 2004/0251419 | A1 | 12/2004 | Nelson et al. |
| 2004/0252810 | A1 | 12/2004 | Tsujii |
| 2005/0094771 | A1* | 5/2005 | Basu .............. A61B 6/583 378/207 |
| 2007/0122020 | A1* | 5/2007 | Claus .............. A61B 6/583 382/131 |
| 2010/0195804 | A1 | 8/2010 | Dafni et al. |
| 2012/0069952 | A1* | 3/2012 | Wu ................ A61B 6/032 378/5 |
| 2014/0153694 | A1* | 6/2014 | Suppes ............. G01T 7/005 378/62 |
| 2014/0211925 | A1 | 7/2014 | Dong et al. |
| 2015/0216498 | A1 | 8/2015 | Schulze et al. |

FOREIGN PATENT DOCUMENTS

| | | |
|---|---|---|
| EP | 2868277 A1 | 5/2015 |
| WO | 2005/015125 A1 | 2/2005 |
| WO | 2010/018537 A1 | 2/2010 |
| WO | 2010/093314 A1 | 8/2010 |
| WO | 2015/044238 A1 | 4/2015 |

OTHER PUBLICATIONS

Bolanos, L., et al. "A digital X-ray imaging system based on silicon strip detectors working in edge-on configuration." Nuclear Instruments and Methods in Physics Research Section A: Accelerators, Spectrometers, Detectors and Associated Equipment 608.3 (2009): 410-416.

* cited by examiner

OBTAINING MEASUREMENT INFORMATION FROM AN EDGE-ON X-RAY DETECTOR AND DETERMINING THE ORIENTATION OF AN EDGE-ON X-RAY DETECTOR WITH RESPECT TO THE DIRECTION OF INCOMING X-RAYS

TECHNICAL FIELD

The proposed technology generally relates to x-ray imaging, and more specifically a method for at least partly determining the orientation of an edge-on x-ray detector with respect to the direction of incoming x-rays, and a method for obtaining measurement information from an edge-on x-ray detector, a method for predicting an effect of movement of an edge-on x-ray detector and/or a focal spot of an x-ray source, and a corresponding system, computer-program, computer-program product and x-ray measurement system.

BACKGROUND

Radiographic imaging such as x-ray imaging has been used for years in medical applications and for non-destructive testing.

Normally, an x-ray imaging system includes an x-ray source and an x-ray detector array consisting of multiple detectors comprising one or many detector elements (independent means of measuring x-ray intensity/fluence). The x-ray source emits x-rays, which pass through a subject or object to be imaged and are then registered by the detector array. Since some materials absorb a larger fraction of the x-rays than others, an image is formed of the subject or object.

An example of a commonly used x-ray imaging system is an x-ray computed tomography, CT, system, which may include an x-ray tube that produces a fan- or cone beam of x-rays and an opposing array of x-ray detectors measuring the fraction of x-rays that are transmitted through a patient or object. The x-ray tube and detector array are mounted in a gantry that rotates around the imaged object. An illustration of a fan beam CT geometry is shown in FIG. 3. For a given rotational position, each detector element measures the transmitted x-rays for a certain projection line. Such a measurement is called a projection measurement. The collection of projection measurements for many projection lines is called a sinogram. The sinogram data is utilized through image reconstruction to obtain an image of the interior of the imaged object. Certain types of image reconstruction, such as iterative reconstruction or basis material decomposition, require the formation of a so-called forward model, which describes the imaging system in detail.

The dimensions and segmentation of the detector array affect the imaging capabilities of the CT apparatus. A plurality of detector elements in the direction of the rotational axis of the gantry, i.e. the z-direction of FIG. 3 enables multi-slice image acquisition. A plurality of detector elements in the angular direction ($\xi$ in FIG. 3) enables measurement of multiple projections in the same plane simultaneously and this is applied in fan/cone-beam CT. Most conventional detectors are so called flat-panel detectors, meaning that they have detector elements in the slice (z) and angular ($\xi$) directions.

X-ray detectors made from low-Z materials need to have a substantial thickness in the direction of the x-ray beam in order to have sufficient detection efficiency to be used in CT. This can be solved by, for example, using an "edge-on" geometry, as in U.S. Pat. No. 8,183,535, in which the detector array is built up of a multitude of detectors, which comprise thin wafers of a low-atomic number material, oriented with the edge towards the impinging x-rays. It is common that each detector has a plurality of detector elements on a 2D grid on the wafer. Each individual wafer is, for example, oriented such that it has detector elements in the slice direction (z) and in the direction of the x-rays, as schematically illustrated in FIG. 3. The edge-on geometry for semiconductor detectors is also suggested in U.S. Pat. No. 4,937,453, U.S. Pat. No. 5,434,417, US 2004/0251419 and WO 2010/093314. Wafer detectors that are oriented with a slight angle with respect to the direction of the x-rays are normally also included in the term "edge-on".

For edge-on detectors to function as designed, it is generally important that the detectors are oriented the way that they are designed for with respect to the direction of the impinging x-rays, or at least that the detectors orientation is known and taken into consideration. Due to uncertainties in the detector mounting and in the position of the focal spot of the x-ray tube, it is not certain that each detector is aligned as desired with respect to the direction of the x-rays. If the detectors are misaligned with respect to the direction of the x-rays and left un-corrected, it can lead to, for example: lower detection efficiency; lower spatial resolution; unaccurate forward models in the image reconstruction; and further, impaired image quality. If the orientation of the detectors with respect to the direction of the x-rays can be estimated, corrections can be made either before or after the image acquisition.

US 2014/0211925, U.S. Pat. No. 8,622,615 and US 2014/0153694 relate to geometric calibration for flat-panel detectors using a calibration phantom or device. However, for conventional flat-panel detectors, the direction of the x-rays does not have a major impact on the performance.

U.S. Pat. No. 5,131,021, U.S. Pat. No. 8,262,288, U.S. Pat. No. 6,370,218, U.S. Pat. No. 5,469,429, U.S. Pat. No. 5,131,021 relate to calibration and/or adjustment of the position of the focal spot of the x-ray tube.

However, nowhere in the prior art are there any described methods for determining parameters related to the orientation of edge-on detectors for CT.

WO 2010/093314 merely mentions the possibility to measure and correct for a mechanical misalignment of a semiconductor detector element that is segmented in the direction of the x-rays based on a model of the expected ratio of detected x-rays in the top and bottom segments.

SUMMARY

It is an object to provide a method for at least partly determining the orientation of an edge-on x-ray detector with respect to the direction of x-rays from an x-ray source.

It is also an object to provide a method for obtaining measurement information from an edge-on x-ray detector having detector elements arranged to enable measuring of x-ray intensity with spatial separation in the direction of x-rays from an x-ray source.

It is another object to provide a method for estimating at least one parameter associated with the orientation of an edge-on x-ray detector with respect to the direction of x-rays.

Yet another object is to provide a method for predicting an effect of movement of an edge-on x-ray detector and/or a focal spot of an x-ray source.

Still another object is to provide a system configured to at least partly determine the orientation of an edge-on x-ray detector with respect to the direction of x-rays from an x-ray source.

It is also an object to provide a computer program for at least partly determining, when executed by a computer, the orientation of an edge-on x-ray detector with respect to the direction of x-rays from an x-ray source.

Another object is to provide a corresponding computer-program product.

It is also an object to provide an improved x-ray measurement system.

These and other objects are met by embodiments of the proposed technology.

The inventors have recognized that the extra dimension of the edge-on detector, due to the extent of the detector in the direction of the x-rays, introduces one or more additional parameters that have to be determined in order to obtain a full geometric description of the imaging setup.

According to a first aspect, there is provided a method for at least partly determining the orientation of an edge-on x-ray detector with respect to the direction of x-rays from an x-ray source. The edge-on detector has detector elements arranged to enable measuring of x-ray intensity with spatial separation in the direction of the x-rays. The method comprises:

obtaining information from measurements, performed by the x-ray detector, representing the intensity of the x-rays at a minimum of two different relative positions of a phantom in relation to the x-ray detector and the x-ray source, the phantom being situated between the x-ray source and the x-ray detector and designed to embed directional information in the x-ray field when exposed to x-rays; and determining at least one parameter associated with the orientation of the x-ray detector with respect to the direction of x-rays based on the obtained information from measurements and a geometrical model of the spatial configuration of the x-ray detector, x-ray source and phantom.

In this way, useful information that can be employed for many different purposes can be obtained in an efficient manner.

By way of example, the parameter(s) associated with the orientation of the x-ray detector can be used for performing system calibrations in terms of, for example, adjustment of the focal spot of the x-ray tube, adjustment of the alignment of individual detectors, improvement of the forward model used in iterative image reconstruction and/or corrections of measured data by post-processing, where post-processing may include interpolation of measured data onto a grid in sinogram space.

According to a second aspect, there is provided a method for obtaining measurement information from an edge-on x-ray detector having detector elements arranged to enable measuring of x-ray intensity with spatial separation in the direction of x-rays from an x-ray source. The method comprises:

providing a phantom, which is designed to embed directional information in the x-ray field when exposed to x-rays, between the x-ray source and the x-ray detector; and inducing relative motion of the phantom in relation to the x-ray detector and the x-ray source; and performing measurements of the intensity of the x-rays at a minimum of two different relative positions of the phantom in relation to the x-ray detector and the x-ray source to obtain the measurement information.

In this way, useful measurement information that can be employed, e.g. for estimating at least one parameter associated with the orientation of an edge-on x-ray detector or for predicting an effect of movement of an edge-on x-ray detector and/or a focal spot of an x-ray source, can be obtained in an efficient manner.

According to a third aspect, there is provided a method for estimating at least one parameter associated with the orientation of an edge-on x-ray detector with respect to the direction of x-rays based on measurement information obtained by the method according to the second aspect.

According to a fourth aspect, there is provided a method for predicting an effect of movement of an edge-on x-ray detector and/or a focal spot of an x-ray source based on based on measurement information obtained by the method according to the second aspect, wherein the measurements are made with different positions of the x-ray detector and/or the focal spot.

According to a fifth aspect, there is provided a system configured to at least partly determine the orientation of an edge-on x-ray detector with respect to the direction of x-rays from an x-ray source. The edge-on detector has detector elements arranged to enable measuring of x-ray intensity with spatial separation in the direction of the x-rays. The system is configured to obtain information from measurements, performed by the x-ray detector, representing the intensity of the x-rays at a minimum of two different relative positions of a phantom in relation to the x-ray detector and the x-ray source, the phantom being situated between the x-ray source and the x-ray detector and designed to embed directional information in the x-ray field when exposed to x-rays. The system is configured to determine at least one parameter associated with the orientation of the x-ray detector with respect to the direction of x-rays based on the obtained information from measurements and a geometrical model of the spatial configuration of the x-ray detector, x-ray source and phantom.

According to a sixth aspect, there is provided a computer program for at least partly determining, when executed by a computer, the orientation of an edge-on x-ray detector with respect to the direction of x-rays from an x-ray source, wherein the edge-on detector has detector elements arranged to enable measuring of x-ray intensity with spatial separation in the direction of the x-rays. The computer program comprises instructions, which when executed by the computer, cause the computer to:

read information from measurements, performed by the x-ray detector, representing the intensity of the x-rays at a minimum of two different relative positions of a phantom in relation to the x-ray detector and the x-ray source, the phantom being situated between the x-ray source and the x-ray detector and designed to embed directional information in the x-ray field when exposed to x-rays; and determine at least one parameter associated with the orientation of the x-ray detector with respect to the direction of x-rays based on the obtained information from measurements and a geometrical model of the spatial configuration of the x-ray detector, x-ray source and phantom.

According to a seventh aspect, there is provided a computer-program product comprising a computer-readable medium having stored thereon a computer program as defined above.

According to an eighth aspect, there is provided an x-ray measurement system comprising:
- an edge-on x-ray detector having detector elements arranged to enable measuring of x-ray intensity with spatial separation in the direction of x-rays from an x-ray source;
- a phantom, which is designed to embed directional information in the x-ray field when exposed to x-rays, arranged between the x-ray source and the x-ray detector,
- wherein relative motion of the phantom can be induced in relation to the x-ray detector and the x-ray source; and
- wherein the x-ray measurement system is configured to perform measurements of the intensity of the x-rays at a minimum of two different relative positions of the phantom in relation to the x-ray detector and the x-ray source to obtain measurement information.

Other advantages will be appreciated when reading the detailed description.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Throughout the drawings, the same reference designations are used for similar or corresponding elements.

According to a first aspect, there is provided a method for at least partly determining the orientation of an edge-on x-ray detector with respect to the direction of x-rays from an x-ray source. The edge-on detector has detector elements arranged to enable measuring of x-ray intensity with spatial separation in the direction of the x-rays.

Figure 1:
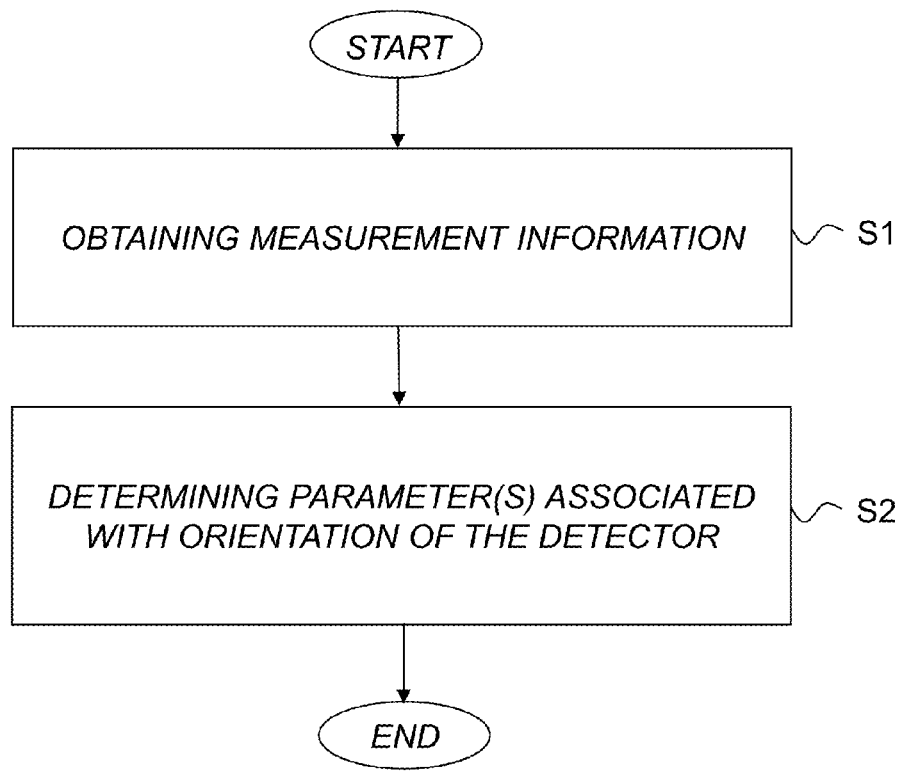
FIG. 1 is a schematic flow diagram illustrating an example of a method for at least partly determining the orientation of an edge-on x-ray detector with respect to the direction of x-rays from an x-ray source according to an embodiment.

With reference to FIG. 1, the method basically comprises the following steps:
S1: obtaining information from measurements, performed by the x-ray detector, representing the intensity of the x-rays at a minimum of two different relative positions of a phantom in relation to the x-ray detector and the x-ray source, the phantom being situated between the x-ray source and the x-ray detector and designed to embed directional information in the x-ray field when exposed to x-rays; and
S2: determining at least one parameter associated with the orientation of the x-ray detector with respect to the direction of x-rays based on the obtained information from measurements and a geometrical model of the spatial configuration of the x-ray detector, x-ray source and phantom.

In this way, useful information that can be employed for many different purposes can be obtained in an efficient manner.

By way of example, the parameter(s) associated with the orientation of the x-ray detector can be used for performing system calibrations in terms of, for example, adjustment of the focal spot of the x-ray tube, adjustment of the alignment of individual detectors, improvement of the forward model used in image reconstruction, and/or corrections of measured data by post-processing.

As an example, the geometrical model may describe the position of the source, the position and orientation of the x-ray detector, the position of the phantom, and geometrical parameters representing a relative motion of the phantom in relation to the x-ray detector and the x-ray source.

In a particular example, the geometrical model is able to predict movement of a trace or shadow from the phantom with respect to the detector. By trace it is meant the intersection of a feature in the x-ray field defined by the phantom and the detector wafer.

Figure 3:
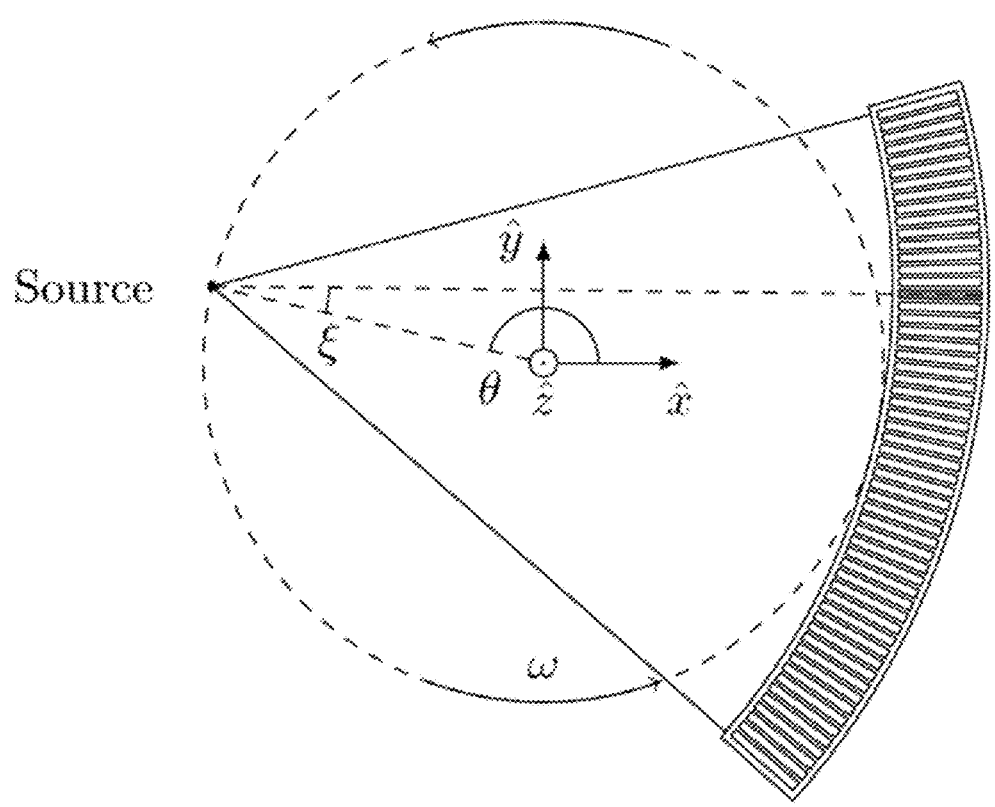
FIG. 3 is a schematic diagram illustrating an example of a fan-beam CT system.

In a basic example, the overall x-ray detector arrangement is normally based on a detector array of multiple edge-on x-ray detectors, which are detector wafers oriented with the edge towards the incoming x-rays. Each detector wafer has detector elements in the so-called slice direction (z in FIG. 3) and also substantially in the direction of the x-rays. Herein, the "detector plane" is typically considered as the plane of the detector wafer.

For example, the parameter(s) associated with the orientation includes at least an angle between the direction of the x-rays and a line in a detector plane defined by a trace of an x-ray beam on the detector, where the x-ray beam is defined by a feature of the phantom.

The parameter(s) associated with the orientation may further include the orientation of said line in said detector plane.

In a particular example, the edge-on detector typically has elements in two directions, wherein one of the directions of the edge-on detector has a component in the direction of the x-rays.

Many different types of so-called phantoms that embed directional information in the x-ray field can be employed. For example, the phantom may comprise at least one hole and/or edge in an x-ray attenuating sheet, or at least one ball bearing. In other words, one or more holes may be defined in the phantom or one or more edges or ball bearings of the phantom may be used.

In a particular example, the determined parameter(s) associated with the orientation of the x-ray detector with respect to the direction of x-rays may be used to improve a forward model used in image reconstruction.

In another example, the determined parameter(s) associated with the orientation of the x-ray detector with respect to the direction of x-rays may be used to localize the focal spot of the x-ray tube.

For example, the method may further comprise the step of finding the optimal position of the focal spot from an image quality perspective.

In yet another example, the determined parameter(s) associated with the orientation of the x-ray detector with respect to the direction of x-rays may be used to adjust an individual x-ray detector in a detector array.

The determined parameter(s) associated with the orientation of the x-ray detector with respect to the direction of x-rays may also be used to deliberately misalign detector elements of the x-ray detector in the direction of the x-rays such that an oversampling in projection space is achieved.

According to a second aspect, there is provided a method for obtaining measurement information from an edge-on x-ray detector having detector elements arranged to enable measuring of x-ray intensity with spatial separation in the direction of x-rays from an x-ray source.

Figure 2:
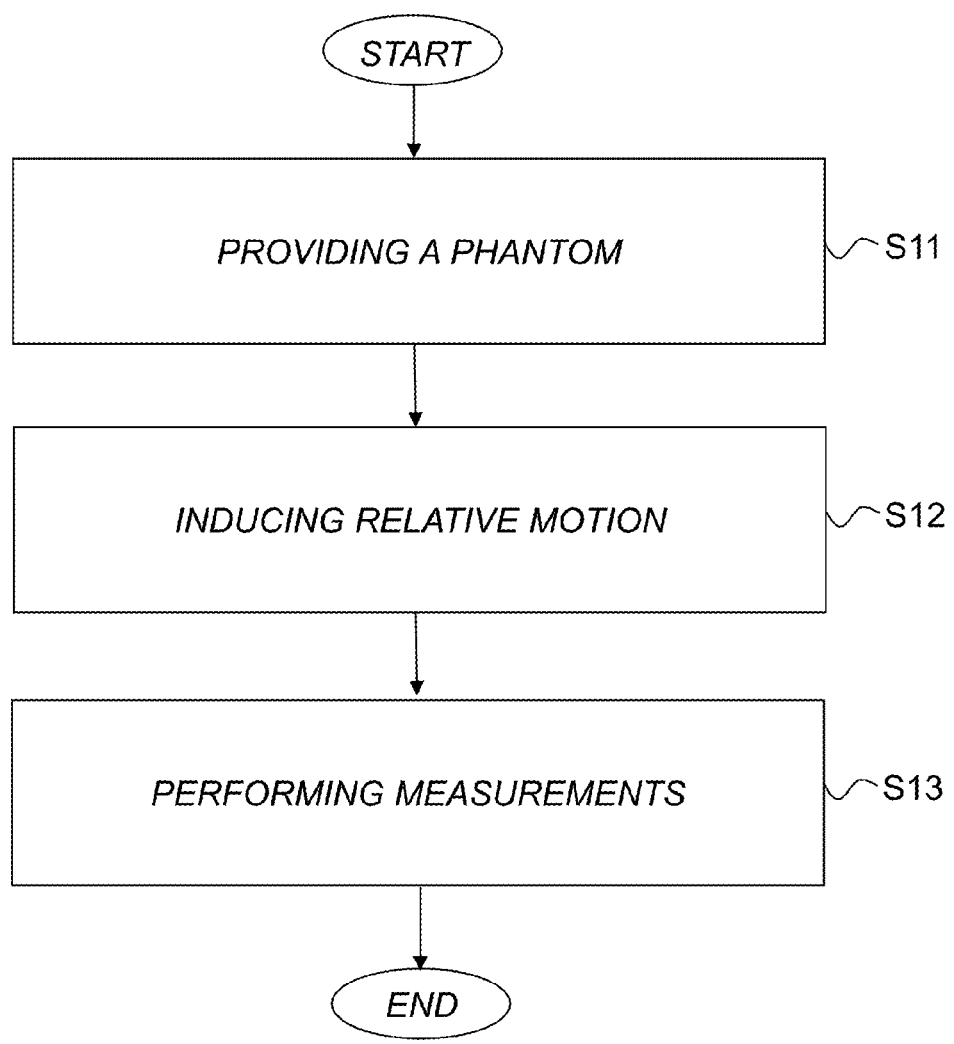
FIG. 2 is a schematic flow diagram illustrating an example of a method for obtaining measurement information from an edge-on x-ray detector according to an embodiment.

With reference to FIG. 2, the method basically comprises the following steps:
S11: providing a phantom, which is designed to embed directional information in the x-ray field when exposed to x-rays, between the x-ray source and the x-ray detector;
S12: inducing relative motion of the phantom in relation to the x-ray detector and the x-ray source; and
S13: performing measurements of the intensity of the x-rays at a minimum of two different relative positions of the phantom in relation to the x-ray detector and the x-ray source to obtain the measurement information.

In this way, useful measurement information that can be employed, e.g. for estimating at least one parameter associated with the orientation of an edge-on x-ray detector or for predicting an effect of movement of an edge-on x-ray detector and/or a focal spot of an x-ray source, can be obtained in an efficient manner.

By way of example, the phantom may comprise at least one hole and/or edge in an x-ray attenuating sheet, or at least one ball bearing.

In a particular example, the relative motion is induced by rotation of a rotational system comprising the x-ray source and the x-ray detector, and/or the relative motion is induced by movement of the phantom.

According to a third aspect, there is provided a method for estimating at least one parameter associated with the orientation of an edge-on x-ray detector with respect to the direction of x-rays based on measurement information obtained by the method according to the second aspect.

By way of example, said at least one parameter associated with the orientation of the x-ray detector with respect to the direction of x-rays is determined based on the obtained measurement information and a geometrical model of the spatial configuration of the x-ray detector, x-ray source and phantom.

In a particular example, the geometrical model describes the position of the source, the position and orientation of the x-ray detector, the position of the phantom, and geometrical parameters representing a relative motion of the phantom in relation to the x-ray detector and the x-ray source.

As an example, the geometrical model is able to predict movement of a trace or shadow from the phantom with respect to the detector.

For example, said at least one parameter associated with the orientation may include at least an angle between the direction of the x-rays and a line in a detector plane defined by a trace of an x-ray beam on the detector, where the x-ray beam is defined by a feature of the phantom.

Optionally, said at least one parameter associated with the orientation further includes the orientation of said line in said detector plane.

In a particular example, the edge-on detector has elements in two directions, wherein one of the directions of the edge-on detector has a component in the direction of the x-rays.

The estimated parameter(s) associated with the orientation of the x-ray detector with respect to the direction of x-rays may be utilized for various purposes.

By way of example, quality of the detector mounting in the gantry may be evaluated based on the estimated parameter(s) associated with the orientation of the x-ray detector with respect to the direction of x-rays.

In another example, input parameters of a forward model of the source/detector system are calibrated based on the estimated parameter(s) associated with the orientation of the x-ray detector with respect to the direction of x-rays.

In yet another example, geometrical parameters describing the spatial configuration of the x-ray source-detector system, such as positions of projection measurements, are calibrated based on the estimated parameter(s) associated with the orientation of the x-ray detector with respect to the direction of x-rays.

It is also possible to perform corrections of x-ray measurement data based on the estimated parameter(s) associated with the orientation of the x-ray detector with respect to the direction of x-rays.

According to a fourth aspect, there is provided a method for predicting an effect of movement of an edge-on x-ray detector and/or a focal spot of an x-ray source based on based on measurement information obtained by the method according to the second aspect, wherein the measurements are made with different positions of the x-ray detector and/or the focal spot.

In a particular example, at least one correction for a position of the x-ray detector, and/or a focal spot of the x-ray source is computed.

For example, said at least one correction may be used as basis for physical adjustments of the position of the x-ray detector, the focal spot, or both.

As an example, a spatial correction of the position of the x-ray source may be computed for simultaneously minimizing a misalignment error of one or many x-ray detectors in a detector array.

In the following, the proposed technology will be described with reference to various non-limiting examples. It should though be understood that the invention is not limited thereto.

In this example embodiment, the detector array is mounted in a CT gantry that rotates about a central axis. The general geometry is described by FIG. 3, where the $\hat{z}$-axis defines the axis of rotation, the $\hat{x}$- and $\hat{y}$-axes define the central slice plane, the angle $\theta$ defines the rotational position of the gantry and the angle $\xi$ defines the position of a detector in the detector array.

The x-ray source is located on one side of the gantry at a distance from the rotational center. The detector array is mounted on the opposite side of the gantry, facing the x-ray source. Both the x-ray source and the detector array rotate with the gantry.

Figure 5:
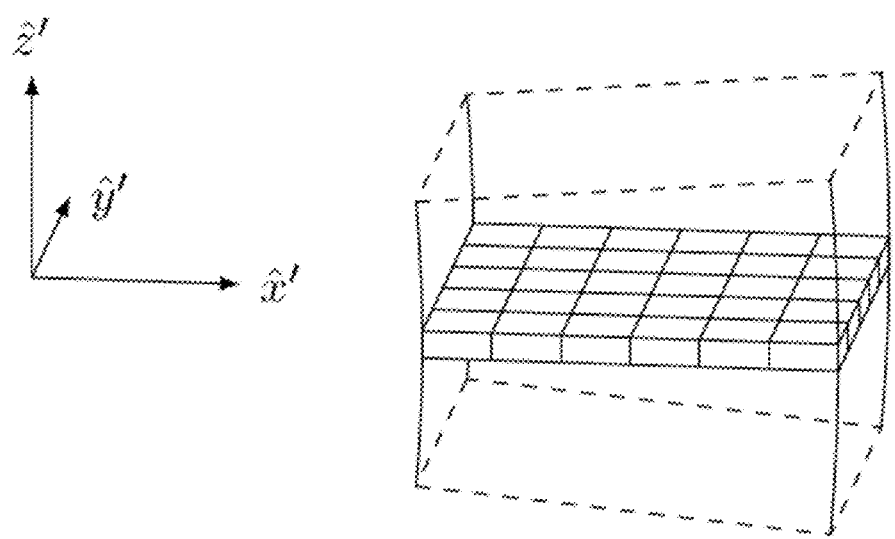
FIG. 5 is a schematic diagram illustrating an example of an edge-on detector displaying a 2D grid of detector elements.

The detectors are, for example, semiconductor wafers with a plurality of pixels in two dimensions (FIG. 5), which are mounted edge-on. The vectors $\hat{x}'$ and $\hat{y}'$ in FIG. 5 lie in the detector plane and $\hat{z}'$ is the normal of the detector plane. An example of an edge-on mounting of the detector is when the source lies on the $\hat{x}'$-axis such that the x-rays travel along the $\hat{x}'$-axis when they hit the middle of the front row of detector.

In this example embodiment of the invention, an x-ray absorbing phantom object is placed stationary at an off-center position inside the gantry. The object can, for example, be a metal sheet with a plurality of holes or a set of highly attenuating beads. The object embeds directional information in the x-ray field by creating "shadows". In other words, the attenuating object creates a gradient in the x-ray field orthogonal to the direction of the x-rays and thus defines the direction of the x-rays by distinguishable features in the gradient of the x-ray field behind the phantom. It is hereinafter assumed, for simplicity only, that the phantom has a single hole defined in a highly attenuating sheet that creates a single beam of x-rays. The phantom is positioned in the gantry such that the radial distance from the hole to the rotational axis is known with highest possible accuracy.

Figure 6:
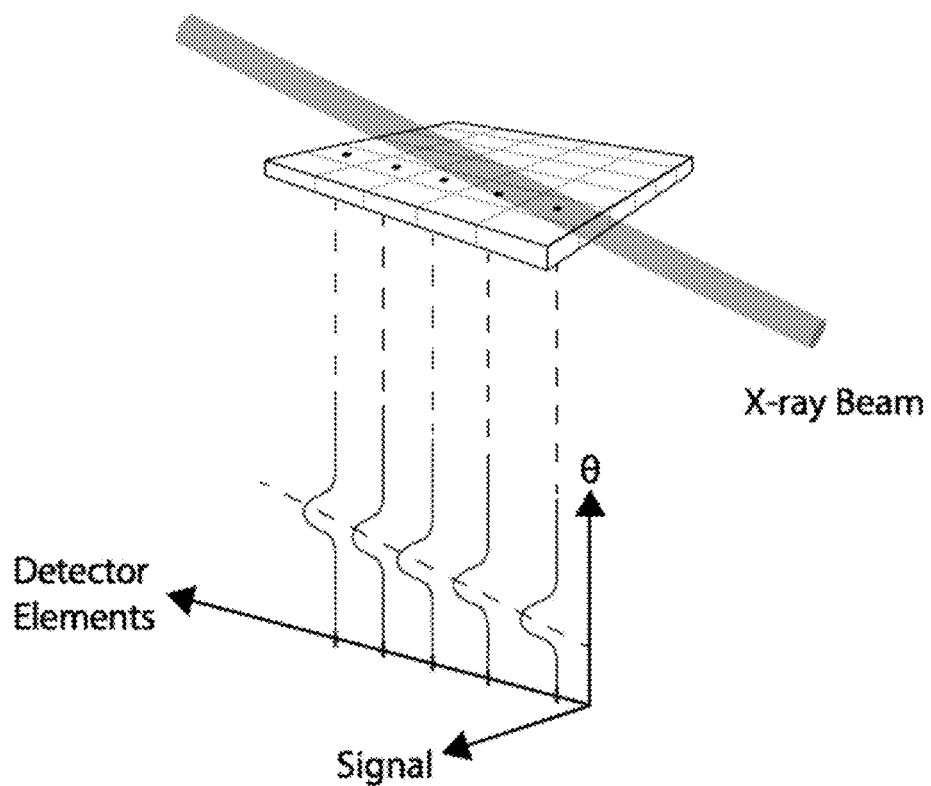
FIG. 6 is a schematic diagram visualizing the data representation from a measurement of the x-ray intensity as a function of gantry rotation angle for each detector element.

When rotating the gantry, and keeping the phantom stationary, the beam of x-rays will move with respect to the detector array due to the off-center position of the hole. Assume now that we perform measurements with the detectors at each rotational position $\theta_k$, where a measurement produces a signal for each detector element proportional to the intensity of the x-rays passing through that detector element. The data representation typically consists of an array of measurements of x-ray intensity for each detector element on the detector for each rotational position $\theta_k$. FIG. 6 visualizes the data representation for the case of a single x-ray beam passing over the detector the gantry rotates.

Figure 7:
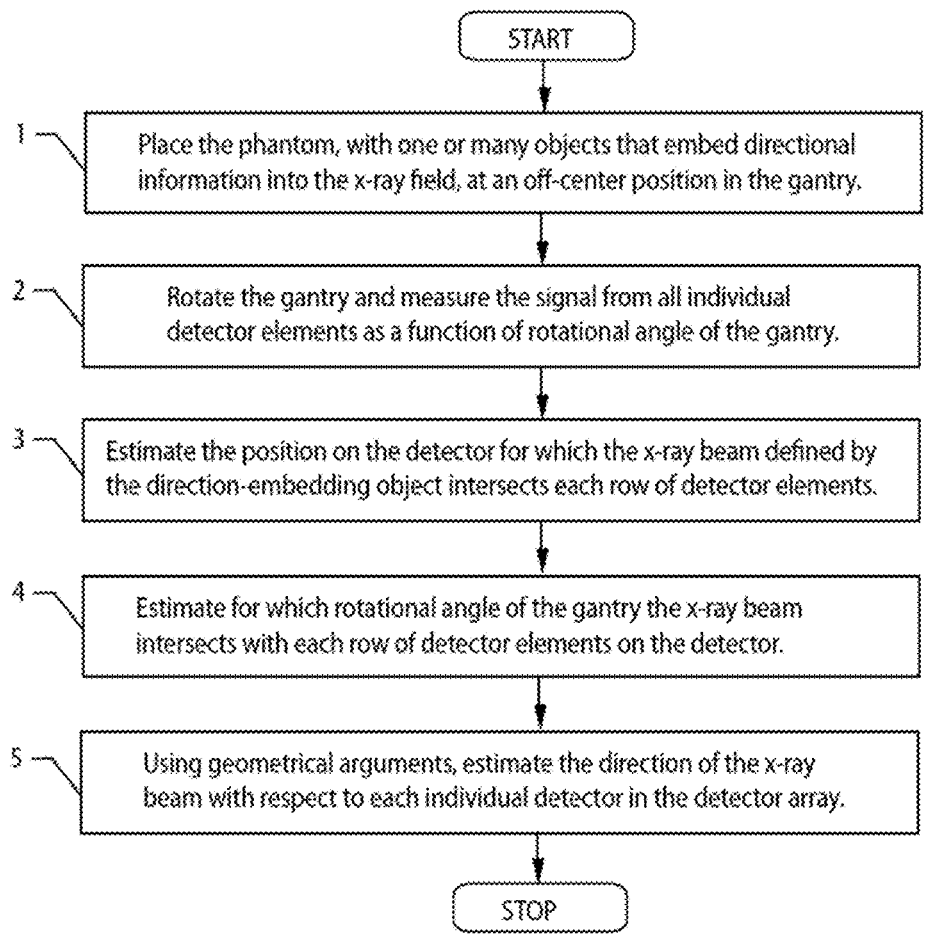
FIG. 7 is a schematic flow diagram of an example method for estimation of the direction of an x-ray beam with respect to an edge-on detector.

The current invention comprises the utilization of the above said measurement to estimate the direction of the x-rays with respect to the detector using geometrical arguments. An example of the method is described by the flow chart in FIG. 7. There are many possible methods for performing the step of estimating the direction of the x-rays with respect to a detector. With reference to FIG. 7, a non-limiting example of such a method is illustrated.

In order to estimate the direction of the x-rays with respect to a detector, assumptions are made regarding the relative position of the detector, the source and the phantom. The position of the focal spot of the x-ray source is modeled with the point $\bar{s}$ and the aligned state of a detector is modeled by a point $\bar{d}$ and two vectors in the detector plane, $\hat{x}'$ and $\hat{y}'$ as in Fig. X, such that the position of each detector element can be expressed as $\bar{d}_{i,j}=\bar{d}+x_i\hat{x}'+y_j\hat{y}'$, where $x_i$ and $y_j$ are known from the model of the detector. For simplicity, the detector elements are assumed to lie on a square grid, however, the described method can readily be adapted to apply when detector elements are not on a square grid. The detector elements with a common x-coordinate will hereinafter be referred to as a detector row. All positions are expressed in a coordinate system that rotates with the gantry such that the detector and the source are stationary. The axis of rotation is defined as the z-axis.

Figure 4:
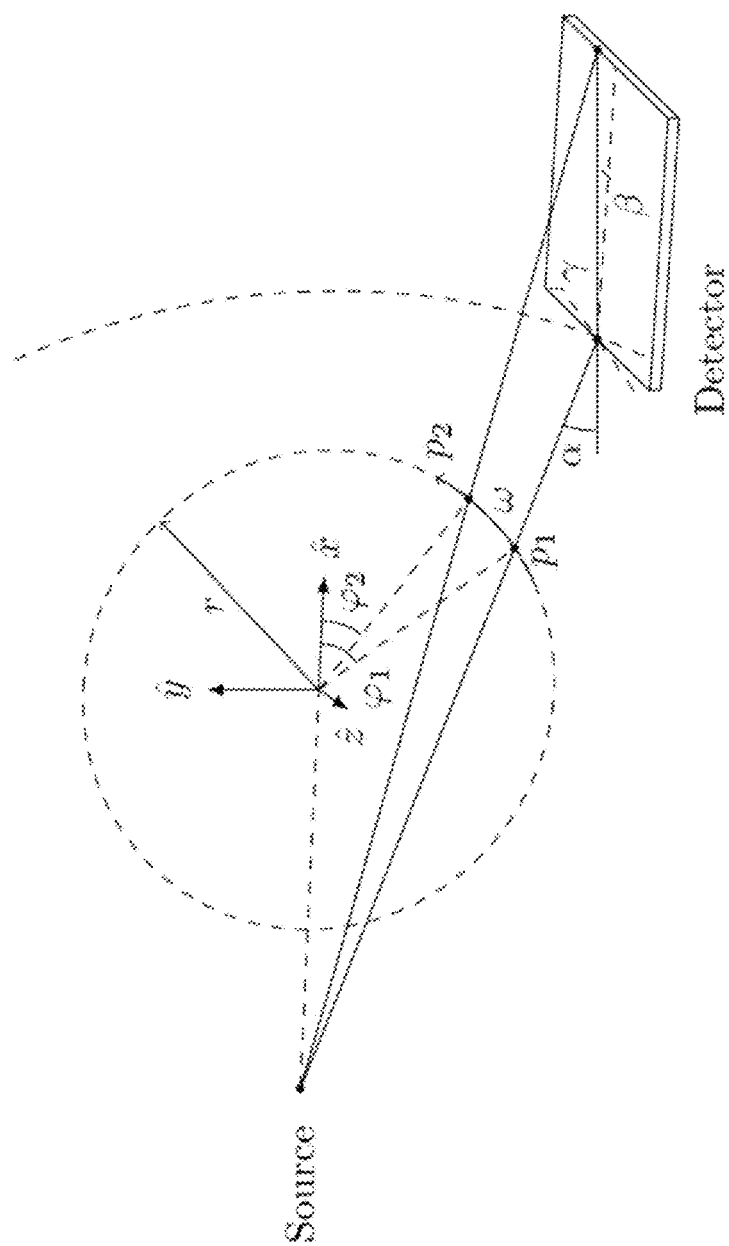
FIG. 4 is schematic diagram illustrating example definitions of detector misalignment.

FIG. 4 displays the definitions of the parameters describing the misalignment of a detector with respect to direction the x-rays that are used here. The direction of the x-rays when they hit the front of the detector is used as reference. The angle $\beta$ describes the orientation of a line approximating the trace of the x-ray beam as it passes through the detector during the rotation of the gantry. The angle $\gamma$ describes the orientation of the detector around the trace of the beam in the detector. The said measurement of x-ray intensity as function of rotational angle is invariant to the angle $\gamma$ if a single beam of x-rays is employed. The angle $\gamma$ can be estimated by, for example, having an edge in the phantom aligned with the rotational axis and comparing when the right and left side of the detector encounters the shadow from the edge. It can be noted, however, that the angle $\gamma$ plays a minor role when it comes to detector performance in terms of energy response and detection efficiency. The hereinafter-described method serves to estimate the angle $\alpha$.

The position of the hole in the phantom is modeled by $\bar{p}(\phi)=[r\cos\phi, r\sin\phi, p_z]^T$ (displayed in FIG. 4 as $p_1$ and $p_2$, which are determined $r$ by $\phi_1$ and $\phi_2$ respectively) and rotates with $\dot{\phi}=-\dot{\theta}=-\omega$ in the rotating coordinate system, where $\omega$ is the angular speed of the gantry. This implies that, for a given $\phi$, the x-rays in the beam created by the hole in the phantom travel along the line $l(\phi)=\bar{s}+k(\bar{p}(\phi)-\bar{s})$ for $k>0$.

Assume that the detector is mounted such that the x-ray beam intersects the i:th row of the detector at $\bar{d}_i$. If the detector is aligned edge-on, the x-ray beam will intersect all rows for the same value of $\theta$. If the detector is misaligned with respect to the source, on the other hand, the x-ray beam will intersect different rows for different values of $\theta$.

First, for each detector row, we determine the position along the row and the rotational angle ($\theta$) for which the intersection of the beam and the row is maximal using, for example, Gaussian fitting on the measured x-ray intensities. Call these values $y_i^*$ and $\theta_i^*$ respectively.

We model the position where the x-ray beam intersects the first detector row by:

$$\bar{d}_1^*=\bar{d}+x_1\hat{x}'+y_1^*\hat{y}'$$

The position of the hole in the phantom ($\bar{p}$) at the moment when the x-ray beam intersects the first detector row has to lie on the line between $\bar{d}_1^*$ and $\bar{s}$, and fulfill $\hat{r}^T\bar{p}_1=r$, where r is the orthogonal distance between the hole in the phantom and the axis of rotation (see FIG. 2). To find $\bar{p}_1$ we solve the equation:

$$\hat{r}^T(\bar{d}_1+q(\bar{s}-\bar{d}_1))=r \qquad (0.1)$$

for q and select the smaller solution for q if the bead is closer to the detector than the source and vice versa. Now $\bar{p}_1$ is given by:

$$\bar{p}_1^*=\bar{d}_1^*+q^*(\bar{s}-\bar{d}_1^*)$$

where $q^*$ come from the solution of (0.1). The position of the hole on the phantom as a function of the measured rotational angle $\theta_i^*$ can be modeled by:

$$\bar{p}_i^*=[r\cos(\phi_1^*+\Delta\theta_i^*), r\sin(\phi_1^*+\Delta\theta_i^*), \hat{z}^T\bar{p}_1^*]^T$$

where the z-component is equal for all i since $\bar{p}$ rotates around the z-axis and $$\Delta\theta_i^* = \theta_i^* - \theta_1^*$$

and $$\varphi_1^* = \cos^{-1}\left(\frac{\hat{x}^T\bar{p}_1^*}{r}\right)$$

The extent of the x-ray beam can be modeled by the line $\bar{l}_i^*=\bar{s}+k(\bar{p}_i^*-\bar{s})$ for $k>0$. The relative lengths between the positions where the x-ray beam and the detector rows intersect are given by $L_{m,n}^*=\sqrt{(x_m-x_n)^2+(y_m^*-y_n^*)^2}$. The positions where the x-ray beam intersects the detector can therefore be obtained by solving the equation:

$$\|\bar{d}_1^*-(\bar{s}+k(\bar{p}_i^*-\bar{s}))\|=L_{1,i}^*$$

for k and estimating the positions where the x-ray beam intersects the detector rows by:

$$\bar{d}_i^* = \begin{cases} \bar{d} + x_1 \hat{x}' + y_1^* \hat{y}', i = 1 \\ \bar{s} + k^*(\bar{p}_i^* - \bar{s}), i = 2, 3, \ldots, n \end{cases}$$

As the hole in the phantom rotates, the beam moves along a cone shaped surface. The size and shape of the cone will depend on the position of the hole with respect to the rotational axis and the source. Considering that the misalignments of the detector is small and that the curvature of the cone can be made very small by appropriate selection of the phantom object, the positions where the beam intersects the detector lie on a straight line to a very good approximation.

Therefore, we can form the directional vector $\bar{v}^*$ that defines the line that fits to the set of points $\bar{d}_i^*$ and lies in the detector plane. The direction of the x-rays when they pass through the point $\bar{d}_1^*$ is given by $\bar{l}_i^*$. The angle $\alpha$ can now be estimated by:

$$\alpha^* = \cos^{-1}(\bar{v}^{*T}\bar{l}_1^*)$$

It can be shown that small errors in the model and/or in the measurements do not substantially affect the result of the method. Since the detector is mounted according to a model of the detector gantry, it is fair to assume that we know the above-mentioned relative positions to fairly high accuracy, within millimeters.

Another example method for utilizing the measurement information relates to the optimal positioning of the focal spot of the x-ray source, i.e. the position that aligns the detector in a true edge on fashion. Similar methods (with some modifications) in which the detector is moved and the focal spot is stationary are also possible. This can be done, e.g. by using the above method if we know the direction with which we can translate the focal spot by a simple calculation. However, the direction with which the focal spot can be translated is not generally known (in the detector coordinate system) and also, the above method uses a model which might induce errors. In this method, we instead trace how the measurements of the beam as it passes the detector change when the focal spot is moved and compute the optimal position of the focal spot without using a geometrical model of the system.

Here we make the assumption that the local motion of the beam with respect to the detector as the beam passes the detector is linear, i.e. the beam is only translated, not rotated. Considering that the detector is generally a thin wafer (approx. 0.5 mm thick) and that it is close to being aligned edge-on to the x-rays, the beam passes the detector very briefly and linearity of motion is a good approximation. However, we do not know, without using a model as in the method described herein, the direction in which the beam is translated with respect to the detector. Also, we do not know the speed with which the beam is translated with respect to the detector.

We introduce a coordinate system $S': \{\hat{x}, \hat{y}, \hat{z}'\}$, where $\hat{z}'$ represents the direction of motion. The axis $\hat{z}'$ can be skew with respect to $\hat{x}$ and/or $\hat{y}$. In this coordinate system, we define the positions where the beam intersects the i:th detector row as $p_i' = (x_i, y_i^*, \theta_i^*)$ (see above for definitions) and the direction of the x-rays in the skew coordinate system v' is given by a linear regression to the points $p_i'$. Now, we measure v' for three different positions of the focal spot: a null position and two translations of the focal spot from the null position in linearly independent directions ($T_1$ and $T_2$). Let's call the measured vectors $v_0'$, $v_1'$ and $v_2'$. The method seeks to find factors $k_1$ and $k_2$ such that the translation of the focal spot $k_1 T_1 + k_2 T_2$ aligns the detector edge-on. The state that aligns the detector edge-on is one where $v' \| \hat{x}$, i.e. the z and y components of v' are zero. In order to predict when this state occurs we observe that the projection of v' onto an x=constant plane moves linearly with the translation of the focal spot to a very good approximation. Therefore, we project the vectors v' onto the x=1 plane by $s = v'/v'^T\hat{x}$ and observe that s as a function of $k_1$ and $k_2$ can be expressed as:

$$s(k_1, k_2) = s_0 + k_1(s_1 - s_0) + k_2(s_2 - s_0)$$

The aligned state is defined by that $s^T \hat{y} = 0$ and $s^T \hat{z} = 0$. We can therefore find the values of $k_1$ and $k_2$ that align the detector by solving the linear equation:

$$\begin{bmatrix} \hat{y}^T(s_1 - s_0) & \hat{y}^T(s_2 - s_0) \\ \hat{z}^T(s_1 - s_0) & \hat{z}^T(s_2 - s_0) \end{bmatrix} \begin{bmatrix} k_1 \\ k_2 \end{bmatrix} = \begin{bmatrix} -\hat{y}^T s_0 \\ -\hat{z}^T s_0 \end{bmatrix}$$

It will be appreciated that the methods and devices described herein can be combined and re-arranged in a variety of ways.

For example, embodiments may be implemented in hardware, or in software for execution by suitable processing circuitry, or a combination thereof.

The steps, functions, procedures, modules and/or blocks described herein may be implemented in hardware using any conventional technology, such as discrete circuit or integrated circuit technology, including both general-purpose electronic circuitry and application-specific circuitry.

Particular examples include one or more suitably configured digital signal processors and other known electronic circuits, e.g. discrete logic gates interconnected to perform a specialized function, or Application Specific Integrated Circuits (ASICs).

Alternatively, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

It should also be understood that it may be possible to re-use the general processing capabilities of any conventional device or unit in which the proposed technology is implemented. It may also be possible to re-use existing software, e.g. by reprogramming of the existing software or by adding new software components.

According to a fifth aspect, there is provided a system configured to at least partly determine the orientation of an edge-on x-ray detector with respect to the direction of x-rays from an x-ray source. The edge-on detector has detector elements arranged to enable measuring of x-ray intensity with spatial separation in the direction of the x-rays. The system is configured to obtain information from measurements, performed by the x-ray detector, representing the intensity of the x-rays at a minimum of two different relative positions of a phantom in relation to the x-ray detector and the x-ray source, the phantom being situated between the x-ray source and the x-ray detector and designed to embed directional information in the x-ray field when exposed to x-rays. The system is configured to determine at least one parameter associated with the orientation of the x-ray detector with respect to the direction of x-rays based on the obtained information from measurements and a geometrical model of the spatial configuration of the x-ray detector, x-ray source and phantom.

Figure 8:
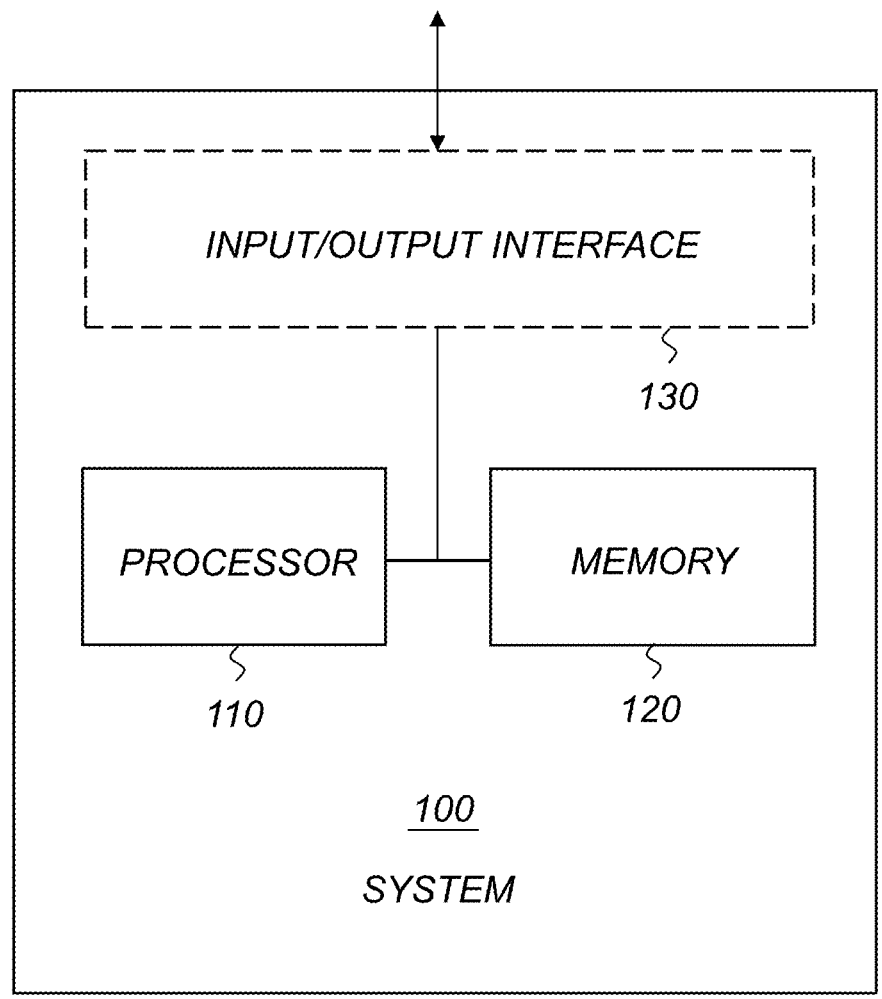
FIG. 8 is a schematic diagram illustrating an example of a system

In a particular example, the system 100 comprises a processor 110 and a memory 120, the memory comprising instructions executable by the processor, whereby the processor is operative to determine the parameter(s) associated with the orientation of the edge-on detector, as illustrated in FIG. 8. Optionally, the system comprises an input/output interface for receiving input data and outputting resulting output data.

In this particular example, at least some of the steps, functions, procedures, modules and/or blocks described herein are implemented in a computer program, which is loaded into the memory for execution by processing circuitry including one or more processors. The processor(s) and memory are interconnected to each other to enable normal software execution. An optional input/output device may also be interconnected to the processor(s) and/or the memory to enable input and/or output of relevant data such as input parameter(s) and/or resulting output parameter(s).

The term 'processor' should be interpreted in a general sense as any system or device capable of executing program code or computer program instructions to perform a particular processing, determining or computing task.

The processing circuitry including one or more processors is thus configured to perform, when executing the computer program, well-defined processing tasks such as those described herein.

The processing circuitry does not have to be dedicated to only execute the above-described steps, functions, procedure and/or blocks, but may also execute other tasks.

Figure 9:
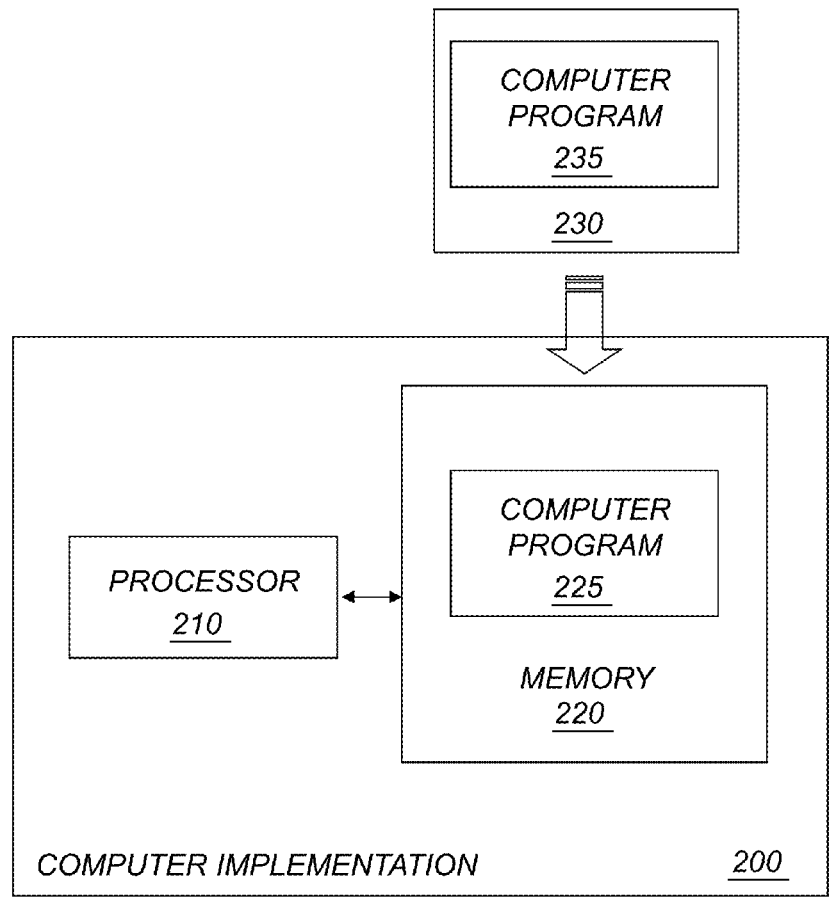
FIG. 9 is a schematic diagram illustrating an example of computer implementation according to an embodiment.

FIG. 9 is a schematic diagram illustrating another example of computer implementation according to an embodiment.

According to a sixth aspect, there is provided a computer program for at least partly determining, when executed by a computer, the orientation of an edge-on x-ray detector with respect to the direction of x-rays from an x-ray source, wherein the edge-on detector has detector elements arranged to enable measuring of x-ray intensity with spatial separation in the direction of the x-rays. The computer program comprises instructions, which when executed by the computer, cause the computer to:

read information from measurements, performed by the x-ray detector, representing the intensity of the x-rays at a minimum of two different relative positions of a phantom in relation to the x-ray detector and the x-ray source, the phantom being situated between the x-ray source and the x-ray detector and designed to embed directional information in the x-ray field when exposed to x-rays; and determine at least one parameter associated with the orientation of the x-ray detector with respect to the direction of x-rays based on the obtained information from measurements and a geometrical model of the spatial configuration of the x-ray detector, x-ray source and phantom.

The proposed technology also provides a computer-program product comprising a computer-readable medium 220; 230 having stored thereon such a computer program.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

The flow diagram or diagrams presented herein may be regarded as a computer flow diagram or diagrams, when performed by one or more processors. A corresponding device, system and/or apparatus may be defined as a group of function modules, where each step performed by the processor corresponds to a function module. In this case, the function modules are implemented as a computer program running on the processor. Hence, the device, system and/or apparatus may alternatively be defined as a group of function modules, where the function modules are implemented as a computer program running on at least one processor.

The computer program residing in memory may thus be organized as appropriate function modules configured to perform, when executed by the processor, at least part of the steps and/or tasks described herein.

Figure 10:
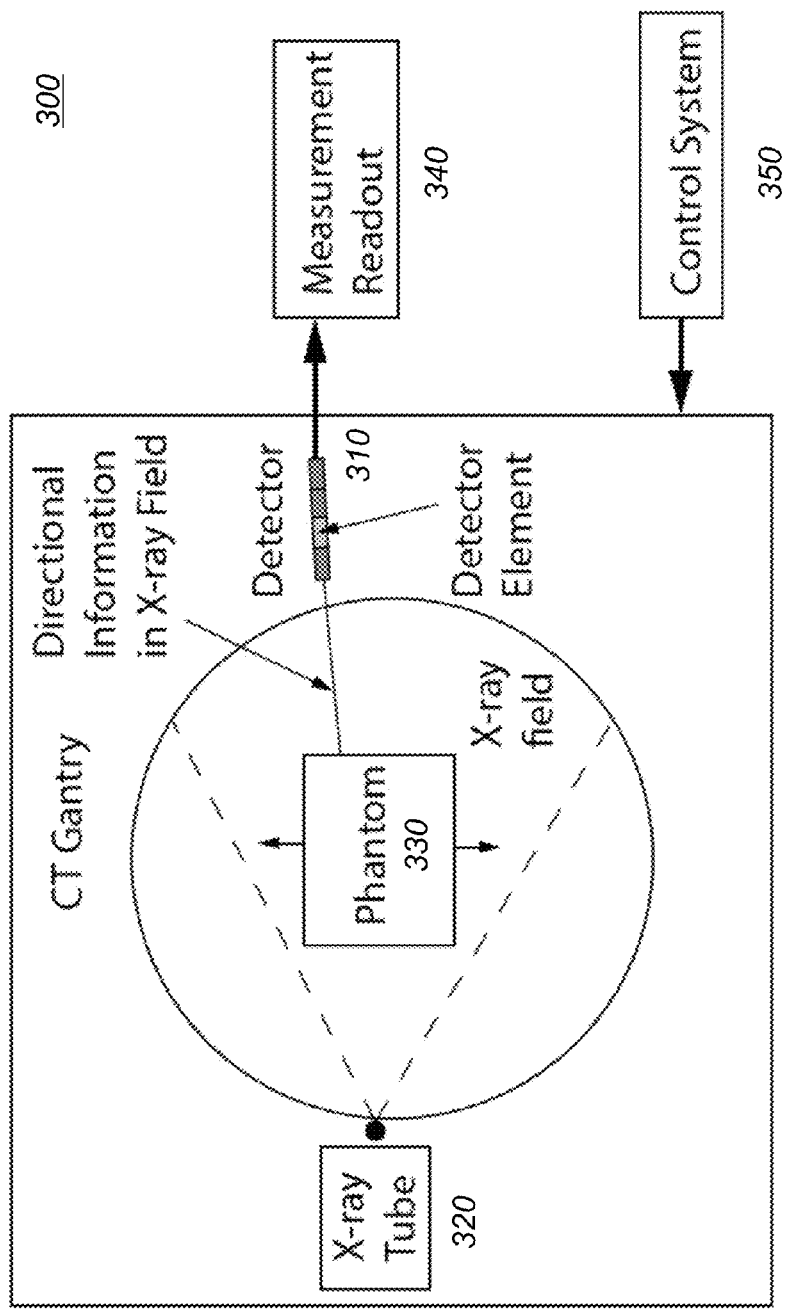
FIG. 10 is a schematic diagram illustrating an example of an x-ray measurement system according to an embodiment.

FIG. 10 is a schematic diagram illustrating an example of an x-ray measurement system according to an embodiment. Basically, the x-ray measurement system 300 comprises:

an edge-on x-ray detector 310 having detector elements arranged to enable measuring of x-ray intensity with spatial separation in the direction of x-rays from an x-ray source 320;

a phantom 330, which is designed to embed directional information in the x-ray field when exposed to x-rays, arranged between the x-ray source and the x-ray detector, wherein relative motion of the phantom can be induced in relation to the x-ray detector and the x-ray source; and wherein the x-ray measurement system 300 is configured to perform measurements of the intensity of the x-rays at a minimum of two different relative positions of the phantom in relation to the x-ray detector and the x-ray source to obtain measurement information.

The x-ray measurement system 300, simply referred to as an x-ray system, may include more than one edge-on x-ray detector, as understood by the skilled person.

In the particular example of FIG. 10, a measurement readout module 340 may be connected to each detector for reading and optionally pre-processing the measurement data and subsequently transferring the measurement data to a computer or similar processing system (not shown in FIG. 10) for computerized processing.

By way of example, the x-ray measurement system 300 may include a control system 350 for effectuating the desired control operations of the system, including inducing the relative motion and/or performing measurements of the intensity of the x-rays at a minimum of two different relative positions.

The embodiments described above are merely given as examples, and it should be understood that the proposed technology is not limited thereto. It will be understood by those skilled in the art that various modifications, combinations and changes may be made to the embodiments without departing from the present scope as defined by the appended claims. In particular, different part solutions in the different embodiments can be combined in other configurations, where technically possible.

The invention claimed is:

1. A method for at least partly determining the orientation of an individual edge-on x-ray detector, forming part of an overall x-ray detector arrangement comprising a detector array of multiple edge-on x-ray detectors, with respect to the direction of x-rays from an x-ray source, the edge-on detector having detector elements in two directions, one of the directions having a component in the direction of the x-rays such that the edge-on detector has detector elements configured to enable measuring of x-ray intensity with spatial separation in the direction of the x-rays, said method comprising:

obtaining information from measurements, performed by the x-ray detector, representing the intensity of the x-rays at a minimum of two different relative positions of a phantom in relation to the x-ray detector and the x-ray source, the phantom being situated between the x-ray source and the x-ray detector and designed to embed directional information in the x-ray field when exposed to x-rays, a measurement producing a signal for each detector element proportional to the intensity of the x-rays passing through the respective detector element; and determining at least one parameter associated with the orientation of the x-ray detector with respect to the direction of x-rays based on the obtained information from measurements and a geometrical model of the spatial configuration of the x-ray detector, x-ray source and phantom.

2. The method of claim 1, wherein the geometrical model describes the position of the source, the position and orientation of the x-ray detector, the position of the phantom, and geometrical parameters representing a relative motion of the phantom in relation to the x-ray detector and the x-ray source.

3. The method of claim 1, wherein the geometrical model is able to predict movement of a trace or shadow from the phantom with respect to the detector.

4. The method of claim 1, wherein said at least one parameter associated with the orientation includes at least an angle between the direction of the x-rays and a line in a detector plane defined by a trace of an x-ray beam on the detector, where the x-ray beam is defined by a feature of the phantom.

5. The method of claim 4, wherein said at least one parameter associated with the orientation further includes the orientation of said line in said detector plane.

6. The method of claim 1, wherein the phantom comprises at least one hole and/or edge in an x-ray attenuating sheet, or comprises at least one ball bearing.

7. The method of claim 1, wherein the determined parameter(s) associated with the orientation of the x-ray detector with respect to the direction of x-rays is/are used to improve a forward model used in image reconstruction.

8. The method of claim 1, wherein the determined parameter(s) associated with the orientation of the x-ray detector with respect to the direction of x-rays is/are used to localize the focal spot of the x-ray tube.

9. The method of claim 8, further comprising finding the optimal position of the focal spot from an image quality perspective.

10. The method of claim 1, wherein the determined parameter(s) associated with the orientation of the x-ray detector with respect to the direction of x-rays is/are used to adjust an individual x-ray detector in a detector array.

11. The method of claim 1, wherein the determined parameter(s) associated with the orientation of the x-ray detector with respect to the direction of x-rays is/are used to perform post-processing of measurement data measured by the x-ray detector.

12. The method of claim 1, wherein the determined parameter(s) associated with the orientation of the x-ray detector with respect to the direction of x-rays is/are used to deliberately misalign detector elements of the x-ray detector in the direction of the x-rays such that an oversampling is achieved.

13. A method for obtaining measurement information from an edge-on x-ray detector forming part of an overall x-ray detector arrangement comprising a detector array of multiple edge-on x-ray detectors, the edge-on detector having detector elements in two directions, one of the directions having a component in the direction of the x-rays such that the edge-on detector has detector elements configured to enable measuring of x-ray intensity with spatial separation in the direction of x-rays from an x-ray source, said method comprising:

providing a phantom, which is configured to embed directional information in the x-ray field when exposed to x-rays, between the x-ray source and the x-ray detector;

inducing relative motion of the phantom in relation to the x-ray detector and the x-ray source; and performing measurements of the intensity of the x-rays at a minimum of two different relative positions of the phantom in relation to the x-ray detector and the x-ray source to obtain the measurement information, a measurement producing a signal for each detector element proportional to the intensity of the x-rays passing through the respective detector element.

14. A method for estimating at least one parameter associated with the orientation of an edge-on x-ray detector with respect to the direction of x-rays based on measurement information obtained by the method of claim 13.

15. The method of claim 14, wherein said at least one parameter associated with the orientation of the x-ray detector with respect to the direction of x-rays is determined based on the obtained measurement information and a geometrical model of the spatial configuration of the x-ray detector, x-ray source and phantom.

16. The method of claim 14, wherein said at least one parameter associated with the orientation includes at least an angle between the direction of the x-rays and a line in a detector plane defined by a trace of an x-ray beam on the detector, where the x-ray beam is defined by a feature of the phantom.

17. The method of claim 14, wherein quality of the detector mounting in the gantry is evaluated based on the estimated parameter(s) associated with the orientation of the x-ray detector with respect to the direction of x-rays.

18. The method of claim 14, wherein input parameters of a forward model of the source/detector system are calibrated based on the estimated parameter(s) associated with the orientation of the x-ray detector with respect to the direction of x-rays.

19. The method of claim 14, wherein geometrical parameters describing the spatial configuration of the x-ray source-detector system, such as positions of projection measurements, are calibrated based on the estimated parameter(s) associated with the orientation of the x-ray detector with respect to the direction of x-rays.

20. The method of claim 14, wherein corrections of x-ray measurement data are performed based on the estimated parameter(s) associated with the orientation of the x-ray detector with respect to the direction of x-rays.

21. A method for predicting an effect of movement of an edge-on x-ray detector and/or a focal spot of an x-ray source based on based on measurement information obtained by the method of claim 13, wherein the measurements are made with different positions of the x-ray detector and/or the focal spot, and at least one correction for a position of the x-ray detector, and/or a focal spot of the x-ray source is computed.

22. A system configured to at least partly determine the orientation of an individual edge-on x-ray detector, forming part of an overall x-ray detector arrangement comprising a detector array of multiple edge-on x-ray detectors, with respect to the direction of x-rays from an x-ray source, the edge-on detector having detector elements in two directions, one of the directions having a component in the direction of the x-rays such that the edge-on detector has detector elements configured to enable measuring of x-ray intensity with spatial separation in the direction of the x-rays,
wherein the system is configured to obtain information from measurements, performed by the x-ray detector, representing the intensity of the x-rays at a minimum of two different relative positions of a phantom in relation to the x-ray detector and the x-ray source, the phantom being situated between the x-ray source and the x-ray detector and designed to embed directional information in the x-ray field when exposed to x-rays, a measurement producing a signal for each detector element proportional to the intensity of the x-rays passing through the respective detector element, and
wherein the system is configured to determine at least one parameter associated with the orientation of the x-ray detector with respect to the direction of x-rays based on the obtained information from measurements and a geometrical model of the spatial configuration of the x-ray detector, x-ray source and phantom.

23. The system of claim 22, wherein the system comprises a processor and a memory, said memory comprising instructions executable by the processor, whereby the processor is operative to determine said at least one parameter associated with the orientation of the x-ray detector with respect to the direction of x-rays.

24. A computer-program product comprising a computer-readable medium having stored thereon a computer program for at least partly determining, when executed by a computer, the orientation of an individual edge-on x-ray detector, forming part of an overall x-ray detector arrangement comprising a detector array of multiple edge-on x-ray detectors, with respect to the direction of x-rays from an x-ray source, the edge-on detector having detector elements in two directions, one of the directions having a component in the direction of the x-rays such that the edge-on detector has detector elements configured to enable measuring of x-ray intensity with spatial separation in the direction of the x-rays, wherein the computer program comprises instructions, which when executed by the computer, cause the computer to:
read information from measurements, performed by the x-ray detector, representing the intensity of the x-rays at a minimum of two different relative positions of a phantom in relation to the x-ray detector and the x-ray source, the phantom being situated between the x-ray source and the x-ray detector and designed to embed directional information in the x-ray field when exposed to x-rays, a measurement producing a signal for each detector element proportional to the intensity of the x-rays passing through the respective detector element; and
determine at least one parameter associated with the orientation of the x-ray detector with respect to the direction of x-rays based on the obtained information from measurements and a geometrical model of the spatial configuration of the x-ray detector, x-ray source and phantom.

25. An x-ray measurement system comprising:
an edge-on x-ray detector forming part of an overall x-ray detector arrangement comprising a detector array of multiple edge-on x-ray detectors, the edge-on detector having detector elements in two directions, one of the directions having a component in the direction of the x-rays such that the edge-on detector has detector elements arranged to enable measuring of x-ray intensity with spatial separation in the direction of x-rays from an x-ray source;
a phantom, which is configured to embed directional information in the x-ray field when exposed to x-rays, arranged between the x-ray source and the x-ray detector,
wherein relative motion of the phantom is able to be induced in relation to the x-ray detector and the x-ray source, and
wherein the x-ray measurement system is configured to perform measurements of the intensity of the x-rays at a minimum of two different relative positions of the phantom in relation to the x-ray detector and the x-ray source to obtain measurement information, a measurement producing a signal for each detector element proportional to the intensity of the x-rays passing through the respective detector element.

* * * * *